(12) United States Patent
Okada

(10) Patent No.: US 9,775,634 B2
(45) Date of Patent: Oct. 3, 2017

(54) BASKET-TYPE GRASPING FORCEPS

(71) Applicant: OLYMPUS CORPORATION, Tokyo (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/070,608

(22) Filed: Mar. 15, 2016

(65) Prior Publication Data

US 2016/0192957 A1 Jul. 7, 2016

Related U.S. Application Data

(63) Continuation of application No. PCT/JP2014/082786, filed on Dec. 11, 2014.

(30) Foreign Application Priority Data

Dec. 12, 2013 (JP) .................................. 2013-257235

(51) Int. Cl.
*A61B 17/221* (2006.01)
*A61B 17/00* (2006.01)

(52) U.S. Cl.
CPC .. *A61B 17/221* (2013.01); *A61B 2017/00292* (2013.01); *A61B 2017/00358* (2013.01); *A61B 2017/2212* (2013.01)

(58) Field of Classification Search
CPC A61B 2017/00358; A61B 2017/00292; A61B 2017/2212; A61B 17/221
See application file for complete search history.

(56) References Cited

U.S. PATENT DOCUMENTS

| 5,496,330 A | * | 3/1996 | Bates | A61B 17/221 606/113 |
|---|---|---|---|---|
| 6,187,017 B1 | | 2/2001 | Gregory, Jr. | |
| 2003/0050663 A1 | * | 3/2003 | Khachin | A61B 17/221 606/200 |
| 2003/0153944 A1 | | 8/2003 | Phung et al. | |
| 2004/0122466 A1 | * | 6/2004 | Bales | A61F 2/013 606/200 |

FOREIGN PATENT DOCUMENTS

| EP | 2 638 870 A1 | 9/2013 |
|---|---|---|
| JP | H09-19438 A | 1/1997 |

(Continued)

OTHER PUBLICATIONS

Mar. 17, 2015 Search Report issued in International Patent Application No. PCT/JP2014/082786.

(Continued)

*Primary Examiner* — Gregory Anderson
*Assistant Examiner* — Christina Lauer
(74) *Attorney, Agent, or Firm* — Oliff PLC

(57) ABSTRACT

In a discharge mechanism of basket-type grasping forceps according to the present invention, a support member can advance and retract relative to a plurality of basket wires, the position of the support member can be fixed, and an object inside a basket part is discharged to the outside of the basket part from a portion of the basket part proximal to the basket wires by movement of the support member and the basket part relative to each other.

7 Claims, 21 Drawing Sheets

(56) References Cited

FOREIGN PATENT DOCUMENTS

| | | |
|---|---|---|
| JP | H11-114070 A | 4/1999 |
| JP | 2001-517527 A | 10/2001 |
| JP | 2005-021195 A | 1/2005 |
| JP | 2006-094876 A | 4/2006 |
| JP | 2006-511266 A | 4/2006 |
| WO | 99/16364 A1 | 4/1999 |
| WO | 2004/056275 A1 | 7/2004 |
| WO | 2012/071620 A1 | 6/2012 |
| WO | 2012/141213 A1 | 10/2012 |

OTHER PUBLICATIONS

Jul. 27, 2017 Extended European Search Report issued in European Patent Application No. 14869235.3.

* cited by examiner

BASKET-TYPE GRASPING FORCEPS

CROSS REFERENCE TO RELATED APPLICATIONS

This application is a continuation application based on a PCT Patent Application No. PCT/JP2014/082786, filed on Dec. 11, 2014, whose priority is claimed on Japanese Patent Application No. 2013-257235, filed Dec. 12, 2013, the entire content of which are hereby incorporated by reference.

BACKGROUND OF THE INVENTION

Field of the Invention

The present invention relates to basket-type grasping forceps.

Description of the Related Art

In the related art, basket-type grasping forceps that are inserted into a duct in the body, such as a bile duct, to collect foreign matter, such as calculus, are known (for example, refer to patent documents: Japanese Unexamined Patent Application, First Publication No. H11-114070; Japanese Unexamined Patent Application, First Publication No. 2006-94876; and PCT International Publication No. WO 2012/141213).

Since the basket-type grasping forceps have a structure that holds foreign matter with a plurality of wires, a basket may not be extracted from a duct, with foreign matter held thereby, in a case where large pieces of foreign matter are collected. For example, if the foreign matter does not come off from between the plurality of wires described in the above patent documents, the basket may not be able to be extracted from the duct.

SUMMARY

According to a first aspect of the present invention, basket-type grasping forceps includes: an insertion section; a plurality of basket wires having a restoring force that restores helically; a basket part that is protrudable and retractable from a distal portion of the insertion section and in which the plurality of basket wires extend helically with a predetermined gap therebetween, the basket part including: a proximal region in which the plurality of basket wires are sparsely arranged; a distal region in which the plurality of basket wires are arranged more closely than in the proximal region; and an internal space surrounded by the proximal region and the distal region; an operating wire that is connected to a proximal end of the basket part and is inserted into the insertion section; a support member that passes through the gap in the basket part and extends substantially parallel to the operating wire; a coupling member that fixes a distal end of the basket part to a distal end of the support member; an operating section that is disposed at a proximal end part of the insertion section in order to advance and retract the operating wire and the support member, respectively; and a discharge mechanism that discharges an object housed in the internal space of the basket part to the outside of the basket part, wherein the discharge mechanism has a first configuration in which the operating wire is relatively retracted along a longitudinal axis of the insertion section with respect to the support member by the operating section, and a second configuration in which the operating wire is relatively advanced along the longitudinal axis of the insertion section with respect to the support member by the operating section, and in the first configuration and the second form, the object housed in the internal space of the basket part is discharged to the outside via the gap in the basket part.

According to a second aspect of the present invention, in the basket-type grasping forceps according to the first aspect, the first configuration in the discharge mechanism may be a state where the basket part is stretched out in an axial direction of the basket part against restoring forces of the plurality of basket wires, and the second configuration in the discharge mechanism may be a state where the basket part is deformed so that the gap in the proximal region of the basket part has a substantial round shape against the restoring forces of the plurality of basket wires.

According to a third aspect of the present invention, in the basket-type grasping forceps according to the first or second aspect, the discharge mechanism may move a proximal end of the basket part in a direction of approach to a distal end of the support member, thereby moving the object inside the basket part from the distal region of the basket part to the proximal region thereof.

According to a fourth aspect of the present invention, in the basket-type grasping forceps according to any one of the first to third aspects, the support member may include: a body wire that is coupled to a distal end of the basket part and extends to the vicinity of a proximal end of the basket part; a first locking part that is fixed to a proximal end of the body wire and has a larger outside dimension than the external diameter of the body wire; and a second locking part that is fixed to the body wire at a position apart from the first locking part further to a distal side than the first locking part and has a larger outside dimension than the external diameter of the body wire, the operating section may include: a restricting member that has a through-hole of a diameter such that the body wire is advanceable and retractable through the through-hole and is disposed between the first locking part and the second locking part in a state where the body wire is inserted through the through-hole; and a restricting wire that has a distal end part fixed to the restricting member and extends to the operating section through the inside of the insertion section, and movement of the body wire to a proximal side with respect to the insertion section may be restricted by fixing the advance/retraction position of the restricting wire in a state where the restricting member abuts against the second locking part, and movement of the body wire to a distal side with respect to the insertion section may be restricted by fixing the advance/retraction position of the restricting wire in a state where the restricting member abuts against the first locking part.

According to a fifth aspect of the present invention, in the basket-type grasping forceps according to any one of the first to third aspects, the basket wires may be made of a shape memory alloy.

According to a sixth aspect of the present invention, in the basket-type grasping forceps according to any one of the first to third aspects, the basket part may include a binding part that binds distal portions of the basket wires, the coupling member may be coupled to a distal side of the binding part with a wire, and the support member may pass through the inside of the basket part at a position offset further in an outer circumferential direction than the centerline of the basket part with respect to the binding part.

DETAILED DESCRIPTION OF THE PREFERRED EMBODIMENTS

First Embodiment

Figure 1:
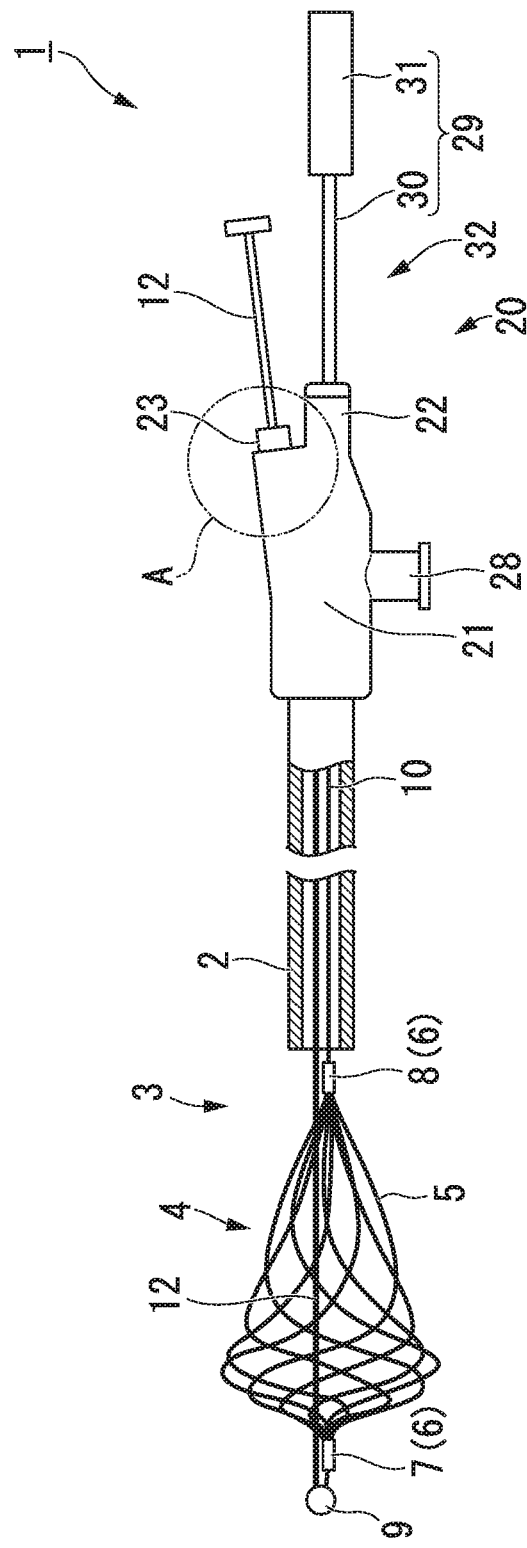
FIG. 1 is a side view illustrating basket-type grasping forceps of a first embodiment of the invention.
Figure 2:
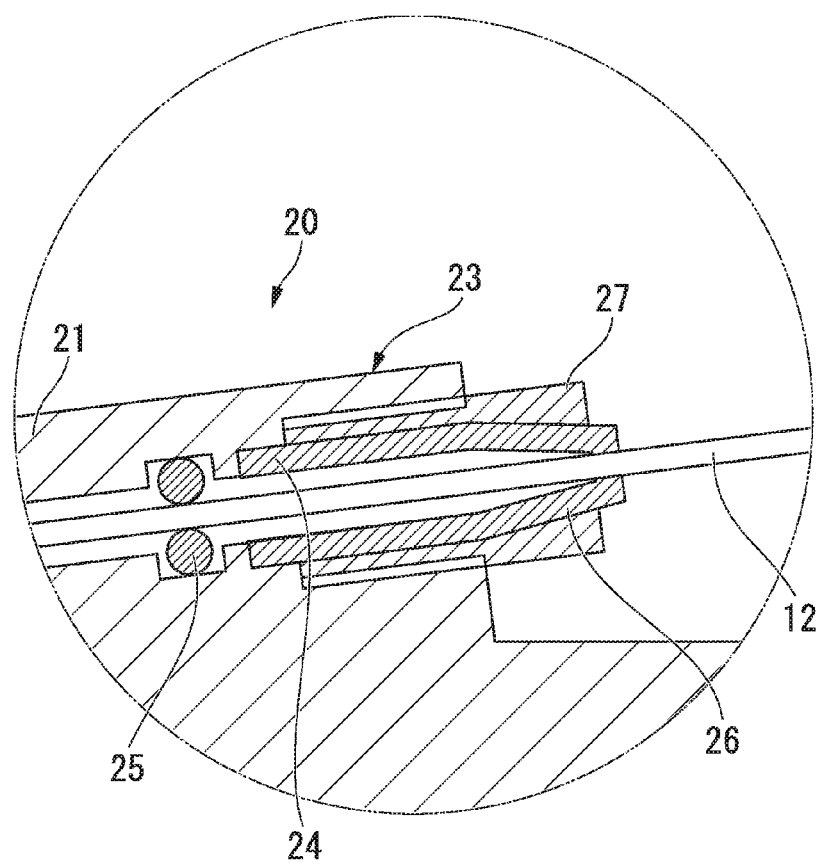
FIG. 2 is an enlarged sectional view of a portion illustrated by symbol A in FIG. 1.

A first embodiment of the invention will be described. FIG. 1 is a side view illustrating basket-type grasping forceps of the present embodiment. FIG. 2 is an enlarged sectional view of a portion illustrated by symbol A in FIG. 1.

Basket-type grasping forceps 1 of the present embodiment illustrated in FIG. 1 is a medical instrument that is inserted into a duct in the body, such as a bile duct, to remove foreign matter.

As illustrated in FIG. 1, the basket-type grasping forceps 1 include a sheath 2 (insertion section), a body section 3 inserted through the sheath 2, and an operating section 20 fixed to the sheath 2.

The sheath 2 is a tube member that has flexibility. The outside dimension of the sheath 2 is such that the sheath is insertable through a treatment tool channel of an endoscope so as to be advanceable and retractable. A distal end of the sheath 2 has hardness such that a basket part 4 (to be described below) can be folded when the basket-type grasping forceps 1 are used.

The body section 3 is an elongated member that has a distal end and a proximal end and is inserted through the sheath 2. The body section 3 includes the basket part 4, an operating wire 10 coupled to the basket part 4, and a center wire 12 (support member) fixed to the basket part 4.

The basket part 4 is disposed on a distal side in the body section 3, spreads substantially in a spindle-like shape in order to hold foreign matter, and is expandable and contractable. The basket part 4 has a substantial linear shape capable of being housed inside the sheath 2 in a contracted state.

The basket part 4 includes a plurality of basket wires 5 and a fixing member 6 for forming the plurality of basket wires 5 in a substantial spindle-like shape.

The plurality of basket wires 5 is disposed at a distal portion of the sheath 2 so as to form a substantial spindle-like shape that hold an object (for example, foreign matter in the body, such as a gallstone) to be removed from the body. In the present embodiment, each of the plurality of basket wires 5 forms a helical shape centered on the centerline of the basket part 4. Additionally, the plurality of basket wires 5 are all configured so that the pitch of the helical shape becomes narrower toward the distal side. That is, the size of openings formed by the plurality of basket wires 5 is the smallest at a distal end of the basket part 4, and is gradually larger toward a proximal side of the basket part 4. Materials for the plurality of basket wires 5 are those that have a restoring force such that a substantial spindle-like shape is maintained by the plurality of basket wires 5 in a state where no external force is applied. In the present embodiment, the plurality of basket wires 5 are respectively formed of shape memory alloys. Specifically, the plurality of basket wires 5 in the present embodiment are made of nickel titanium alloys.

The fixing member 6 has a distal fixing member 7 (binding part) that binds and fixes the respective basket wires 5 on the distal side of the basket part 4, and a proximal fixing member 8 that binds and fixes the respective basket wires 5 on the proximal side of the basket part 4. The distal fixing member 7 and the proximal fixing member 8 all have a tubular shape. All the basket wires 5 are inserted through the inside of each of the distal fixing member 7 and the proximal fixing member 8. The distal fixing member 7 and the basket wires 5 are fixed together by well-known fixing methods, such as bonding, brazing, soldering, or welding. The proximal fixing member 8 and the basket wires 5 are fixed together by well-known fixing methods, such as bonding, brazing, soldering, or welding.

Moreover, the basket part 4 has a tip member 9 that couples the distal end of the basket part 4 and a distal end of the center wire 12. The tip member 9 is a substantial spherical member in which a distal end has a curved surface shape. A wire extending from the distal end of the basket part 4 and the center wire 12 are respectively fixed to a proximal end of the tip member 9 in an inserted state. In this state, the distal fixing member 7 is located on the centerline of the basket part 4 serving as a binding part for distal portions of the basket wires 5, and the center wire 12 is arranged so as to pass through the inside of the basket part 4 at a position offset further in an outer circumferential direction than the centerline of the basket part 4 with respect to the distal fixing member 7.

The operating wire 10 is disposed on the proximal side of the basket part 4 and is fixed to the basket part 4. The operating wire 10 and the basket part 4 are fixed together by well-known fixing methods, such as bonding, brazing, soldering, or welding.

The center wire 12 is connected to the distal end of the basket part 4 and is inserted through the inside of the sheath 2 via the inside of the basket part 4. In the present embodiment, the center wire 12 is fixed together with the respective basket wires 5 inside the tip member 9 of the basket part 4. Regarding the connection between the center wire 12 and the basket part 4, the basket wires 5 may extend to the distal fixing member 7, and the tip member 9 and the distal fixing member 7 may be connected together with a separate connecting wire. Additionally, in the present embodiment, a proximal region of the center wire 12 is inserted into the sheath 2 from an opening on the distal end side of the sheath 2, extends to the operating section 20 through the inside of the sheath 2, and protrudes from the inside of the operating section 20 to the outside of the operating section 20.

As illustrated in FIGS. 1 and 2, the operating section 20 is provided at a proximal end of the sheath 2 in order to advance and retract each of the operating wire 10 and the center wire 12 with respect to the sheath 2. The operating section 20 is fixed to the proximal end of the sheath 2.

The operating section 20 includes an operation body 21 and a slider 29.

The operation body 21 is fixed to the proximal end of the sheath 2. The operation body 21 has a first port 22 through which a portion of the slider 29 for advancing and retracting the operating wire 10 is inserted, and a second port 23 through which the center wire 12 is inserted.

The first port 22 is a port through which a shaft 30 to be described below is capable of being advanced and retracted in a watertight state.

The second port 23 has an opening 24 that communicates with the sheath 2, a plug 26 that is disposed within the opening 24 and has elasticity, and a screw body 27 that is screwed into the opening 24 of the second port 23 and elastically deforms the plug 26, and has the function as a chuck for fixing the position of the center wire 12 in contact with an outer peripheral surface of the center wire 12. Additionally, a circular O ring 25, which has an inside dimension such that the O-ring comes into contact with an outer surface of the center wire 12, is provided in the opening 24 of the second port 23, and is brought into a watertight state. In addition, the second port 23 may be configured so that the position of the center wire 12 is fixed by methods other than the chuck fixing.

When the center wire 12 is in a fixed state in the second port 23, the center wire 12 is immovable with respect to the operating section 20, and if the fixed state of the center wire 12 is released in the second port 23, the center wire 12 is advanceable/retractable and rotatable with respect to the operating section 20.

In the present embodiment, a discharge mechanism 32 for moving foreign matter or the like within the basket part 4 or the like from the distal side in the basket part 4 to the proximal side thereof by the operating wire 10, the center wire 12, the first port 22, and the second port 23 and discharging the foreign matter or the like to the outside of the basket part 4 is configured.

In addition, the operating section 20 in the present embodiment has a third port 28 for liquid-feeding, for example, liquids, such as a contrast medium or cleaning water. The third port 28 communicates with the sheath 2 through the inside of the operation body 21. If a liquid is injected from the third port 28 in a state where the first port 22 and the second port 23 are brought into a watertight state, the liquid flows into the inside of the sheath 2 and is discharged from the opening on the distal end side of the sheath 2.

The slider 29 has a shaft 30 fixed to a proximal end of the operating wire 10, and a grip 31 disposed at a proximal end of the shaft 30.

The shaft 30 is a rigid member, and is cylindrical in the present embodiment. The operating wire 10 and the shaft 30 are coupled together via, for example, a tubular member (not illustrated). In the present embodiment, the operating wire 10 and the shaft 30 may be fixed together by well-known fixing methods, such as bonding, brazing, soldering, or welding.

The grip 31 is a member that is formed to be thicker than the outer shape of the shaft 30 so as to be easily gripped by an operator of the basket-type grasping forceps 1. The grip 31 may have an antislip device if necessary.

Next, how to use the basket-type grasping forceps 1 of the present embodiment, and the operation of the basket-type grasping forceps will be described. FIGS. 3 to 7 are views for describing how to use the basket-type grasping forceps of the present embodiment.

The basket-type grasping forceps 1, similar to a general basket type medical treatment tool, is inserted into ducts, such as a bile duct in a patient's body, through an endoscope channel, in a state where the basket part 4 is housed in the sheath 2. If the basket part 4 is protruded from the sheath 2 within a duct by the advance operation of the slider 29, the basket part 4 is expanded due to the elastic force of the basket wires 5. After foreign matter 35 (refer to FIG. 3), such as calculus, is collected in the expanded basket part 4, the slider 29 can be pulled to reduce the diameter of the basket part 4, and the foreign matter 35 can be firmly held within the basket part 4. Thereafter, the basket-type grasping forceps 1 is extracted from the inside of the patient's body together with the endoscope, and the foreign matter 35 is collected.

In a case where the foreign matter 35 held within the basket part 4 is large, the basket part 4 may not be removed from ducts, such as a bile duct. In order to avoid this, it is necessary to discharge the held foreign matter 35 out of the basket in a state where the basket part 4 is located within a duct. As related-art methods for removing the foreign matter 35, there are methods, such as introducing an urgent lithotripter, a laser, or the like into the inside of the body, and breaking the foreign matter 35. However, these related-art methods are complicated and become a cause that increases the time required for entire treatment.

Figure 3:
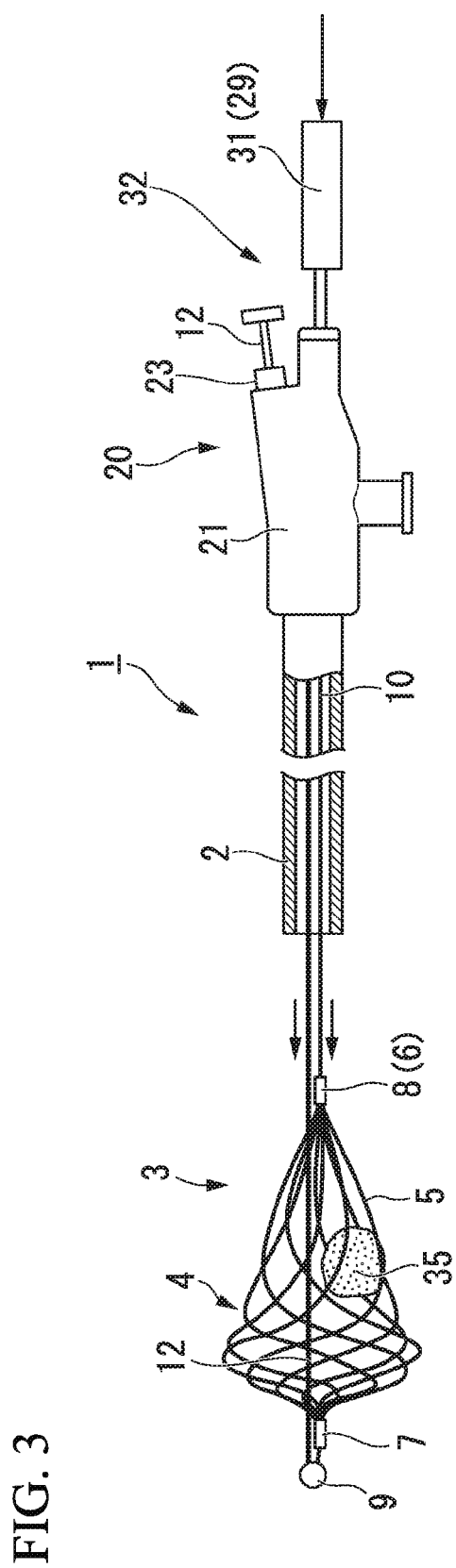
FIG. 3 is a view for describing how to use the basket-type grasping forceps.

In the basket-type grasping forceps 1, first, as illustrated in FIG. 3, the operating wire 10 is advanced to move the basket part 4 to the front. In this case, the center wire 12 coupled to the distal end of the basket part 4 also moves to the front together with the basket part 4. In this case, by shaking the basket part 4 forward and backward, the foreign matter 35 held on the distal side of the basket part 4 may move to the proximal side of the basket part 4. Additionally, the foreign matter 35 is apt to move to the proximal side of the basket part 4 in a state where the distal end of the basket part 4 is turned to the upper side. Additionally, in a case where a space where the foreign matter 35 is present is filled with a body fluid (for example, bile or the like), the basket part 4 may be moved forward, and thereby the body fluid may cause resistance against the movement of the foreign matter 35 and push out the foreign matter 35 to the proximal side of the basket part 4.

In this way, the foreign matter 35 moves from the distal side of the basket part 4 to the proximal side thereof through the operation of moving the basket part 4 to the front within a duct. That is, the foreign matter 35 inside the basket part 4 moves the basket part 4 from a region where the basket wires 5 of the basket part 4 are dense to a region where the basket wires are sparse through the operation of moving the basket part 4 to the front within the duct.

Figure 4:
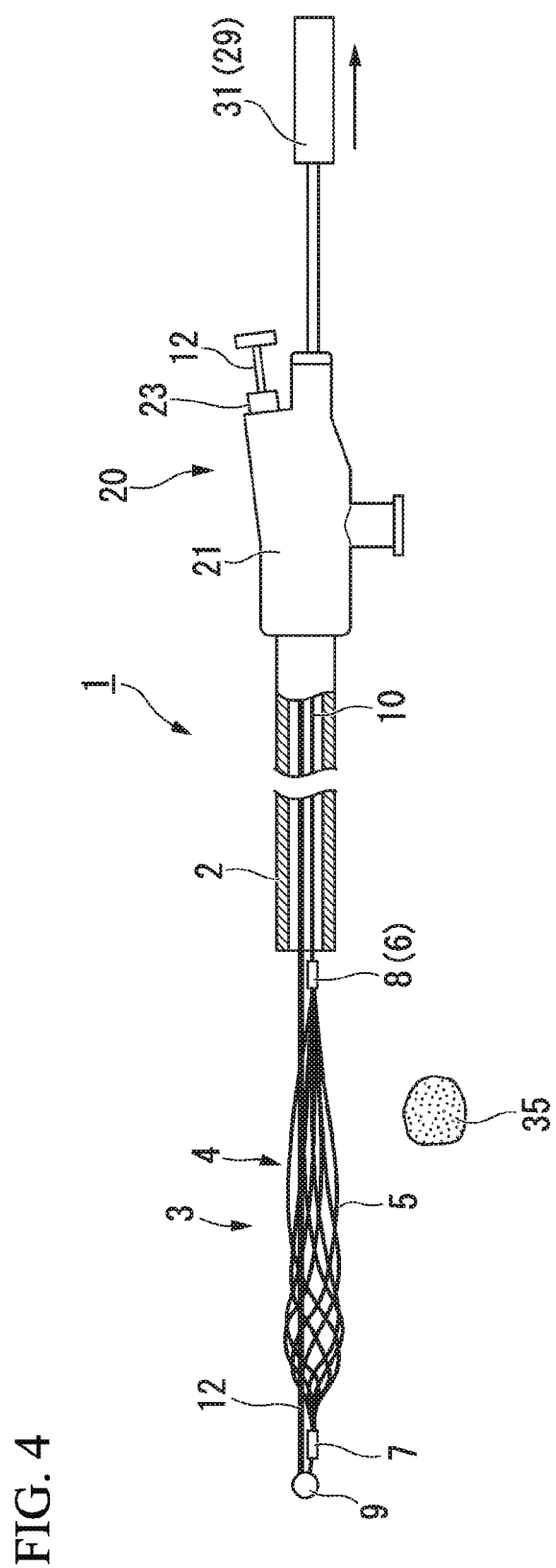
FIG. 4 is a view for describing how to use the basket-type grasping forceps.

Subsequently, the operator engages the plug 26 with the outer peripheral surface of the center wire 12 in the second port 23, and fixes the position of the center wire 12 to the operating section 20. Moreover, as illustrated in FIG. 4, the operator operates the slider 29 to retract the operating wire 10. Then, the basket part 4 moves relative to the center wire 12 so that the proximal end of the basket part 4 is moved to the proximal side by the operating wire 10 without changing the position of the distal end of the center wire 12. Accordingly, the basket part 4 is brought into a state where the basket part is stretched out, and the space capable of containing the foreign matter 35 becomes gradually narrower due to the stretch-out of the basket part 4. Since the foreign matter 35 within the basket part 4 is in the region where the respective basket wires 5 are sparse on the proximal side of the basket part 4, the foreign matter 35 is discharged from a gap between the basket wires 5 in a proximal portion of the basket part 4 to the outside of the basket part 4 due to reduction of the space capable of containing the foreign matter 35.

In this way, in the present embodiment, the basket wires 5 can move the foreign matter 35 from the region where the basket wires 5 are dense to the region where the basket wires 5 are sparse. Moreover, by stretching out the basket wires 5 in a forward-backward direction, the basket part 4 can be reduced in the radial direction, and accordingly, the foreign matter 35 can be discharged from a portion the basket wires 5 are sparse in the proximal portion of the basket part 4. As a result, the basket-type grasping forceps 1 of the present embodiment can easily remove the foreign matter 35 held by the basket wires 5, and can enhance the efficiency of treatment.

Next, another method of discharging the foreign matter 35 from the basket part 4 in the basket-type grasping forceps 1 of the present embodiment, and the operation of the basket-type grasping forceps 1 in a case where this method is used will be described.

Figure 5:
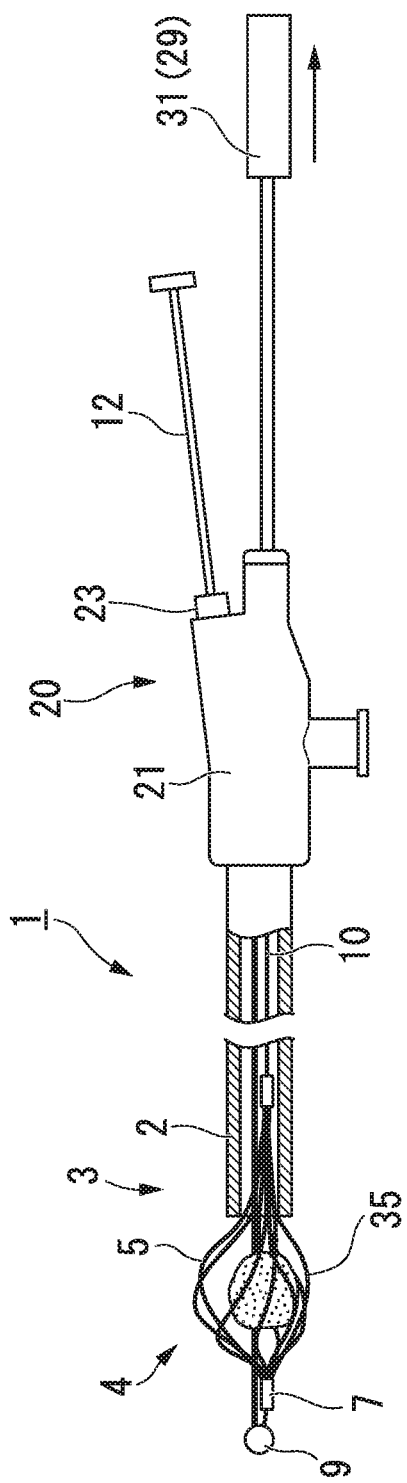
FIG. 5 is a view for describing how to use the basket-type grasping forceps.
Figure 6:
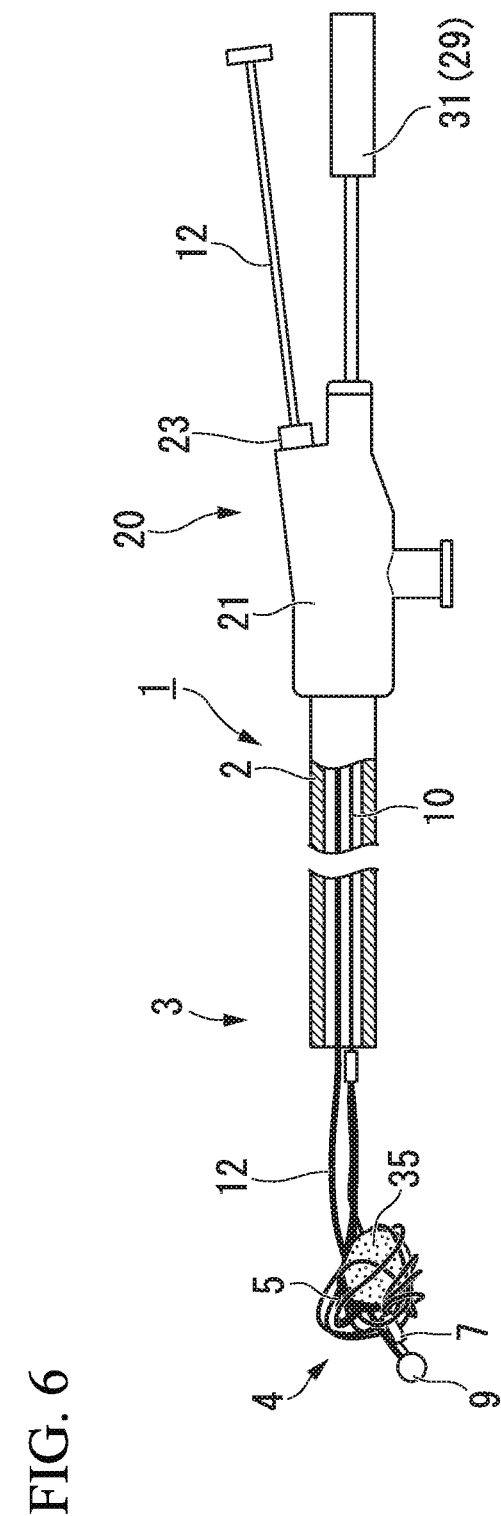
FIG. 6 is a view for describing how to use the basket-type grasping forceps.
Figure 7:
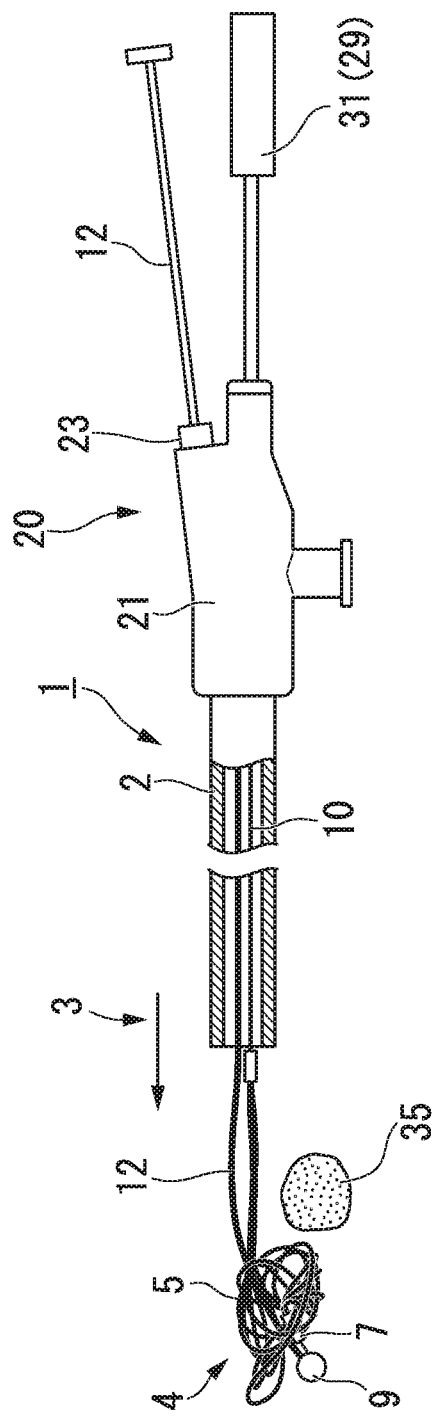
FIG. 7 is a view for describing how to use the basket-type grasping forceps.

In a case where the foreign matter 35 is held by a distal portion of the basket part 4 inside the basket part 4 and is not pulled out of ducts, such as a bile duct, as illustrated in FIG. 5, the basket part 4 is retracted to a degree such that a portion of the proximal portion of the basket part 4 enters the sheath 2, instead of moving the basket part 4 to the front in the above use method. In this case, the center wire 12 is also retracted by retraction of the basket part 4. Subsequently, the position of the center wire 12 is fixed in the second port 23, and the operating wire 10 is moved to the front in a state where the center wire 12 does not move. As illustrated in FIG. 6, the position of the distal end of the basket part 4 is to stay at the position of the distal end of the center wire 12, and the position of the proximal end of the basket part 4 is moved to the front by the operating wire 10. Accordingly, a substantial spindle-like shape in the basket wires 5 collapses, and the gaps between the basket wires 5 open in the proximal portion of the basket part 4. The gaps that open in the proximal portion of the basket part 4 become substantial circular openings with an internal diameter allowing passage of the foreign matter 35. By moving the entire basket-type grasping forceps 1 to the front in this state, as illustrated in FIG. 7, the foreign matter 35 within the basket part 4 moves relatively toward the proximal side of the basket part 4 through the openings formed by deformation of the basket wires 5, and is discharged to the outside of the basket part 4.

In this way, the basket-type grasping forceps 1 of the present embodiment is configured so that the proximal end of the basket part 4 can be moved to the proximal side or the distal side in a state where the position of the distal end of the basket part 4 is fixed by the center wire 12. For this reason, in the basket-type grasping forceps 1 of the present embodiment, the basket part 4 can be stretched out in a case where the proximal end of the basket part 4 is moved to the proximal side, and contrary to this, the substantial spindle-like shape of the basket part 4 can be collapsed when the proximal end of the basket part 4 is moved to the distal side. As a result, in the basket-type grasping forceps 1 of the present embodiment, the foreign matter 35 inside the basket part 4 can be easily discharged to the proximal side of the basket part 4.

Second Embodiment

Figure 8:
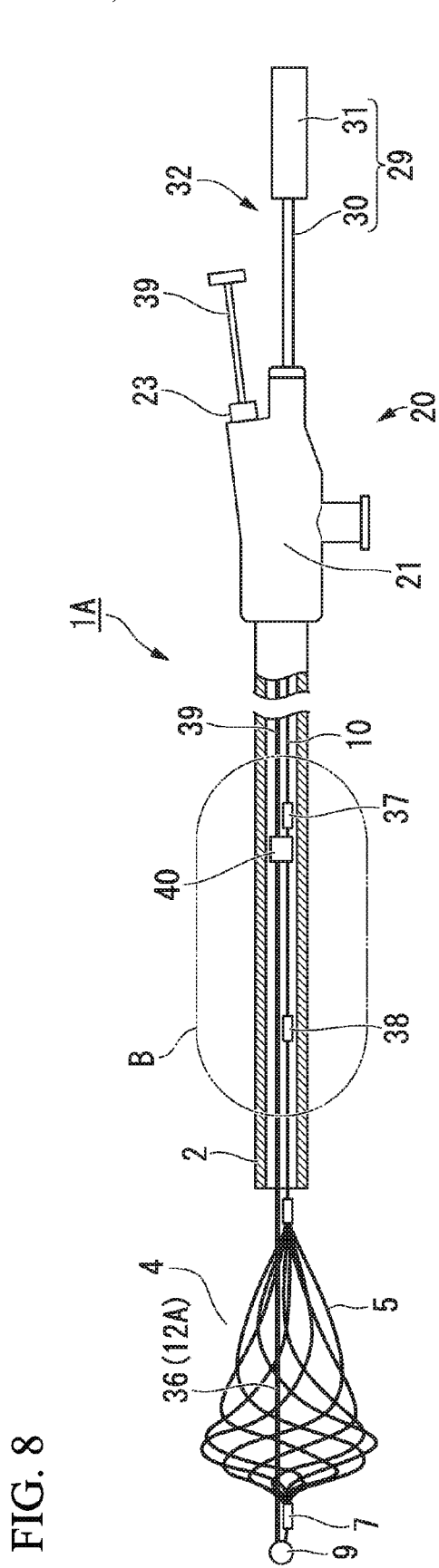
FIG. 8 is a partial sectional view illustrating basket-type grasping forceps of a second embodiment of the invention.
Figure 9:
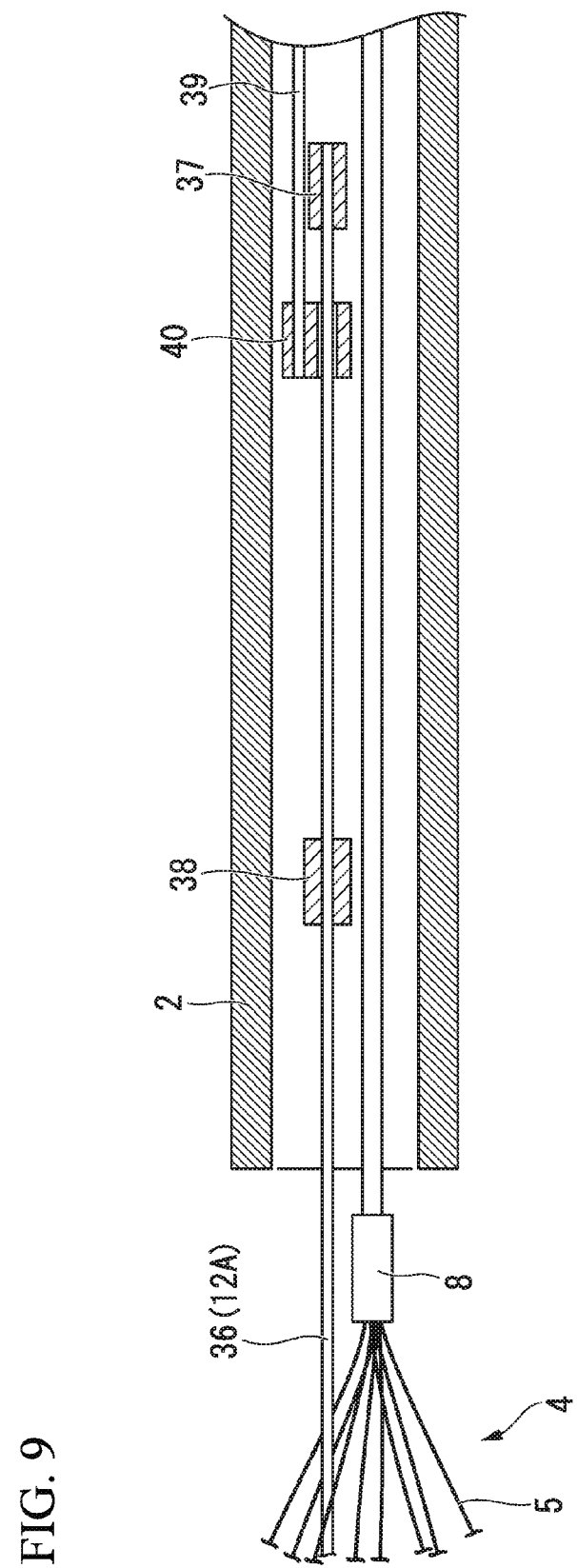
FIG. 9 is an enlarged sectional view of a portion illustrated by symbol B in FIG. 8.

Next, a second embodiment of the invention will be described. In addition, in respective embodiments to be described below, the same constituent elements as those of the above first embodiment will be designated by the same reference numerals as those of the first embodiments, and duplicate description will be omitted. FIG. 8 is a partial sectional view illustrating basket-type grasping forceps of the present embodiment. FIG. 9 is an enlarged sectional view of a portion illustrated by symbol B in FIG. 8.

As illustrated in FIGS. 8 and 9, basket-type grasping forceps 1A of the present embodiment include a center wire 12A with a different configuration instead of the center wire 12 described in the first embodiment. Additionally, in the present embodiment, a restricting wire 39 coupled to the center wire 12A of the present embodiment within the sheath 2 is disposed in the operating section 20 described in the first embodiment instead of the proximal region of the center wire 12 described in the first embodiment.

The center wire 12A has a body wire 36 that is coupled to the distal end of the basket part 4 and extends to the vicinity of the proximal end of the basket part 4, and a first locking part 37 and a second locking part 38 fixed to a proximal portion of the body wire 36. The first locking part 37 and the second locking part 38 are arranged so as to be separated from each other.

A distal end of the body wire 36 is fixed to the proximal end of the tip member 9, similar to the first embodiment. A proximal end of the body wire 36 is inserted into the inside of the sheath 2 from a distal opening of the sheath 2.

The first locking part 37 is fixed to the proximal end of the body wire 36. The outside dimension of the first locking part 37 is larger than the external diameter of the body wire 36. The first locking part 37 is provided in order to transmit operating capability from the restricting wire 39 as a restricting member 40 to be described below abuts thereagainst when the body wire 36 is moved backward using the restricting wire 39. Additionally, the first locking part 37 functions as a retainer that maintains the coupled state between the body wire 36 and the restricting wire 39.

The second locking part 38 is fixed to the body wire 36 at a position separated by a predetermined distance from the proximal end of the body wire 36 to the distal side. The outside dimension of the second locking part 38 is larger than the external diameter of the body wire 36. The second locking part 38 is provided in order to transmit operating capability from the restricting wire 39 as the restricting member 40 to be described below abuts thereagainst when the body wire 36 is moved forward using the restricting wire 39.

The distance between the first locking part 37 and the second locking part 38 is separated only by a distance equal to or more than a movement distance required for being brought into a state where the basket part 4 is protruded from the distal end of the sheath 2 until the basket part 4 is fully opened from a state where the basket part 4 is housed within the sheath 2. The distance between the first locking part 37 and the second locking part 38 is set according to the shape of the basket part 4.

The restricting wire 39 is provided in the operating section 20. The position of a proximal end of the restricting wire 39 is fixed by the second port 23 described in the first embodiment when the plug 26 abuts against an outer peripheral surface of the restricting wire 39. The restricting member 40 for coupling a distal end of the restricting wire 39 between the first locking part 37 and the second locking part 38 is fixed to the distal end of the restricting wire 39.

The restricting member 40 has a through-hole with a diameter such that the body wire 36 is advanceable and retractable, and is disposed between the first locking part 37 and the second locking part 38 in a state where the body wire 36 is inserted through the through-hole.

The operation of the basket-type grasping forceps 1A of the present embodiment will be described. FIGS. 10 to 17 are views for describing how to use the basket-type grasping forceps of the present embodiment.

Figure 10:
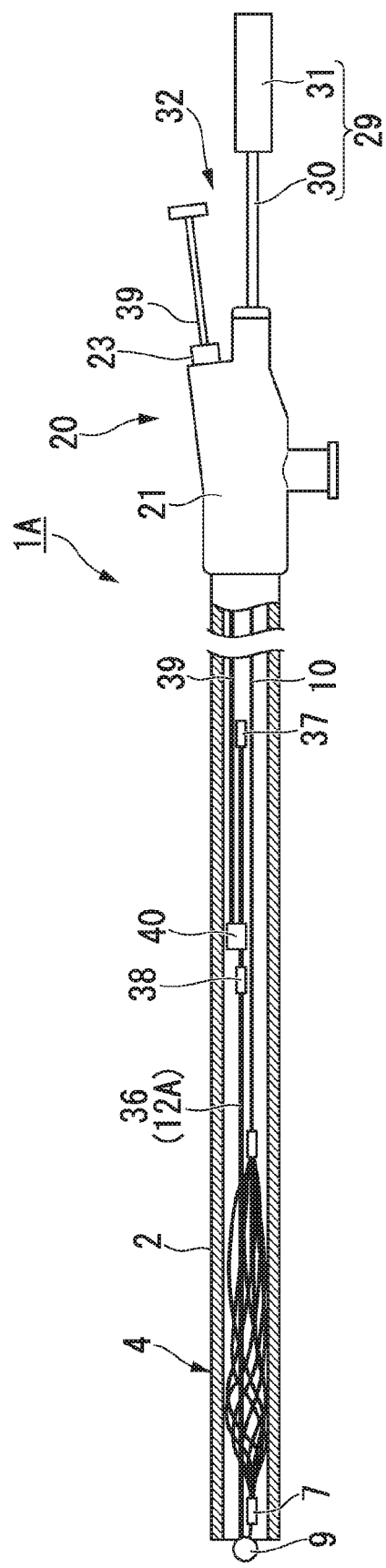
FIG. 10 is a view for describing how to use the basket-type grasping forceps.

In the present embodiment, as illustrated in FIG. 10, in a state the basket part 4 is housed within the sheath 2, the restricting member 40 is at a position separated from the first locking part 37 to the front side, and the restricting wire 39 is fixed by the plug 26 of the second port 23.

Figure 11:
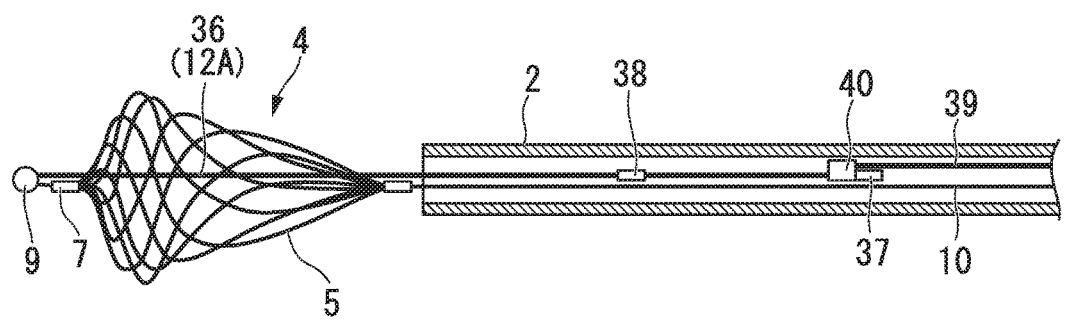
FIG. 11 is a view for describing how to use the basket-type grasping forceps.
Figure 12:
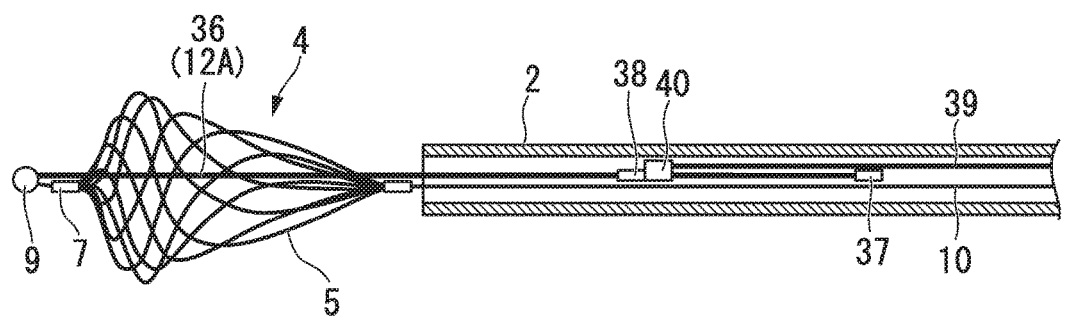
FIG. 12 is a view for describing how to use the basket-type grasping forceps.

In this state, if the operating wire 10 is moved forward by the operator after the basket-type grasping forceps 1A is inserted into the body, as illustrated in FIG. 11, the basket part 4 is protruded from the distal opening of the sheath 2 to the front. In this case, the center wire 12A is advanced together with the basket part 4. Additionally, since the body wire 36 of the center wire 12A is advanceable and retractable with respect to the restricting member 40, the restricting wire 39 does not move in the process in which the body wire 36 moves forward together with the basket part 4. However, the restricting member 40 of the distal end of the restricting wire 39 does not cause resistance against the movement of the body wire 36.

By fixing the advance/retraction position of the restricting wire 39 in a state (refer to FIG. 11) where the restricting member 40 abuts against the first locking part 37, the movement of the body wire 36 to the distal side with respect to the sheath 2 is restricted. By fixing the advance/retraction position of the restricting wire 39 in a state (refer to FIG. 12) where the restricting member 40 abuts against the second locking part 38, the movement of the body wire 36 to the proximal side with respect to the sheath 2 is restricted.

When the foreign matter 35 is housed inside the basket part 4 in the basket-type grasping forceps 1A of the present embodiment, in a case where the foreign matter 35 is held by the distal portion of the basket part 4, similar to the above first embodiment, the foreign matter 35 is moved from the distal portion of the basket part 4 to the proximal portion of the basket part 4 using a method described below, and the foreign matter 35 is discharged to the outside of the basket part 4.

Figure 13:
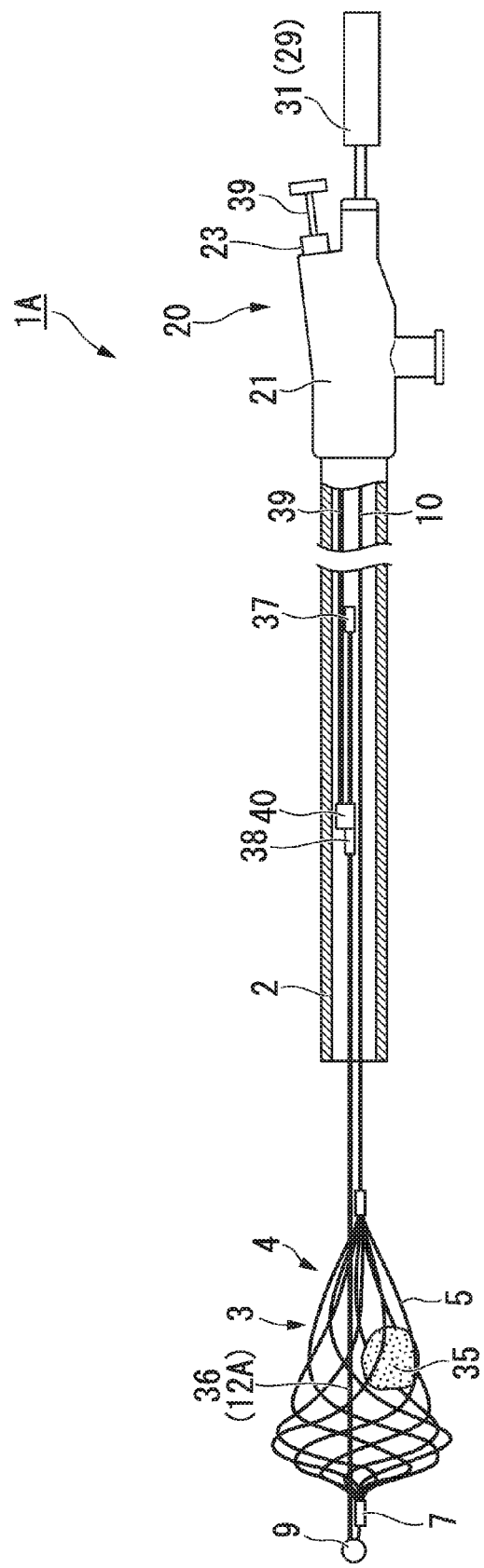
FIG. 13 is a view for describing how to use the basket-type grasping forceps.
Figure 14:
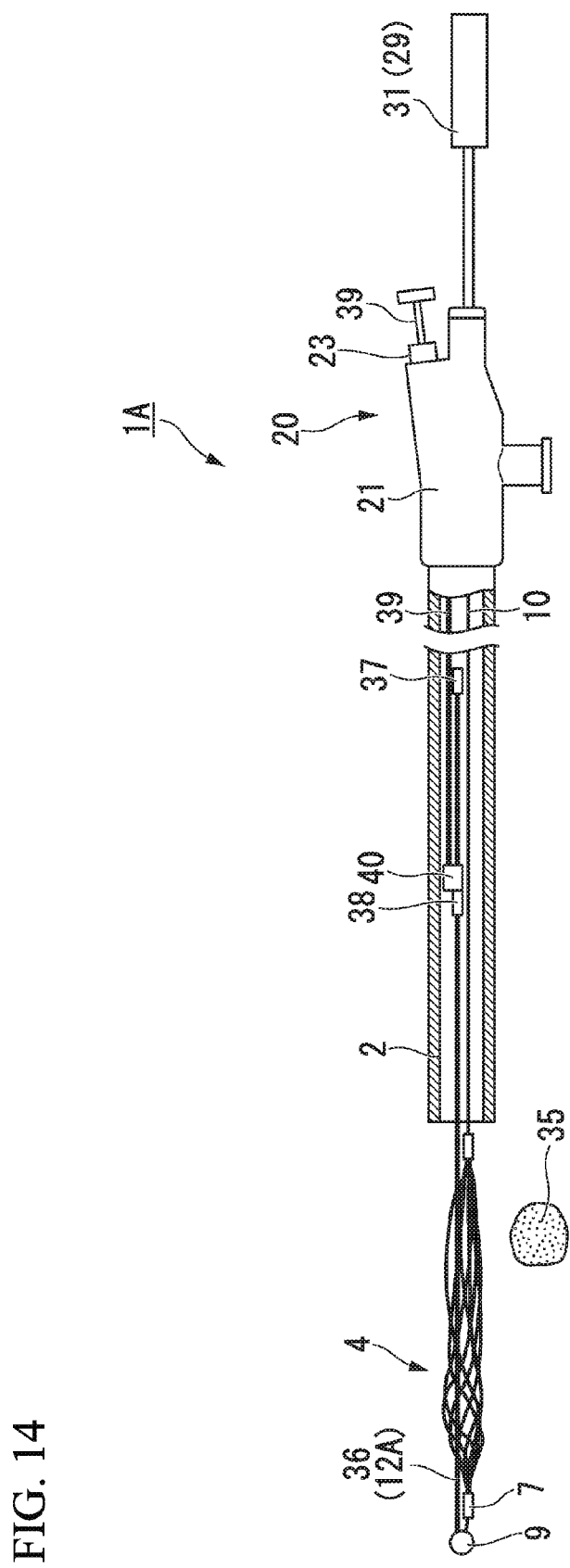
FIG. 14 is a view for describing how to use the basket-type grasping forceps.

Specifically, as described in the first embodiment, in order to stretch out the basket part 4 in the forward-backward direction, first, as illustrated in FIG. 13, the restricting wire 39 is fixed in the second port 23 in a state where the restricting wire 39 is advanced and the restricting member 40 abuts against the second locking part 38 of the center wire 12A. Subsequently, as illustrated in FIG. 14, the operating wire 10 is retracted and the proximal end of the basket part 4 is moved to the proximal side. Accordingly, the position of the distal end of the basket part 4 is maintained by the body wire 36, and the position of the proximal end of the basket part 4 is moved to the proximal side by the operating wire 10. As a result, the basket part 4 is stretched out with the movement of the operating wire 10 to the proximal side. Accordingly, in the proximal portion of the basket part 4, the foreign matter 35 is discharged from the gap between basket wires 5 to the outside of the basket part 4.

Figure 15:
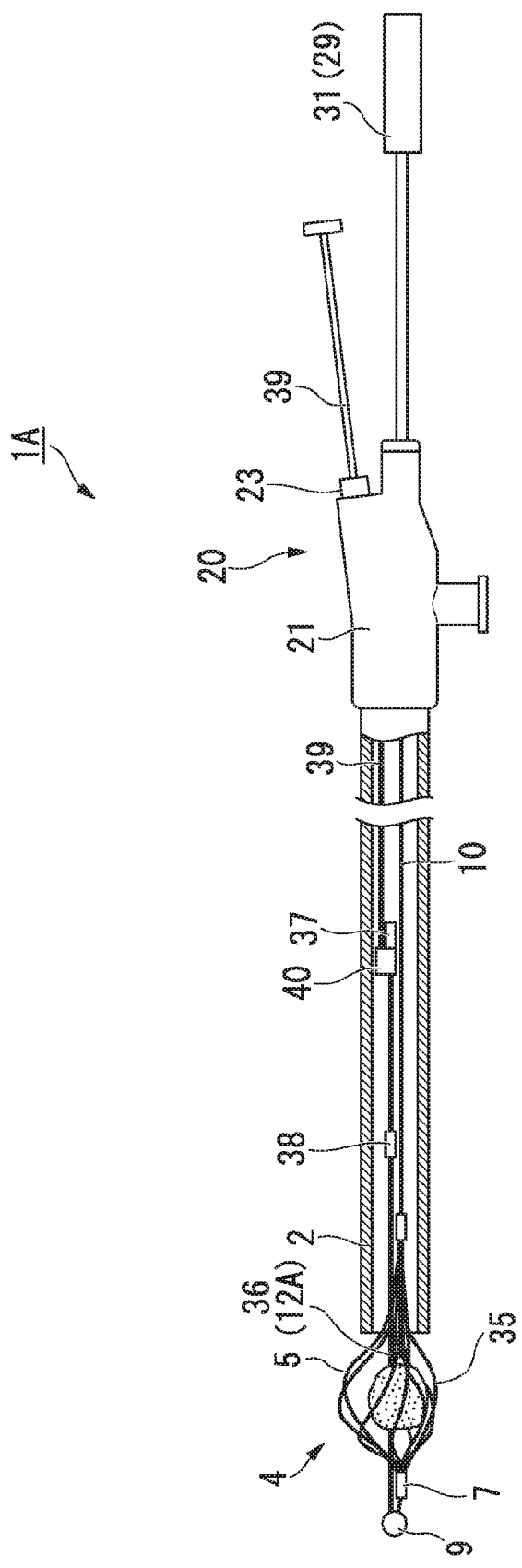
FIG. 15 is a view for describing how to use the basket-type grasping forceps.
Figure 16:
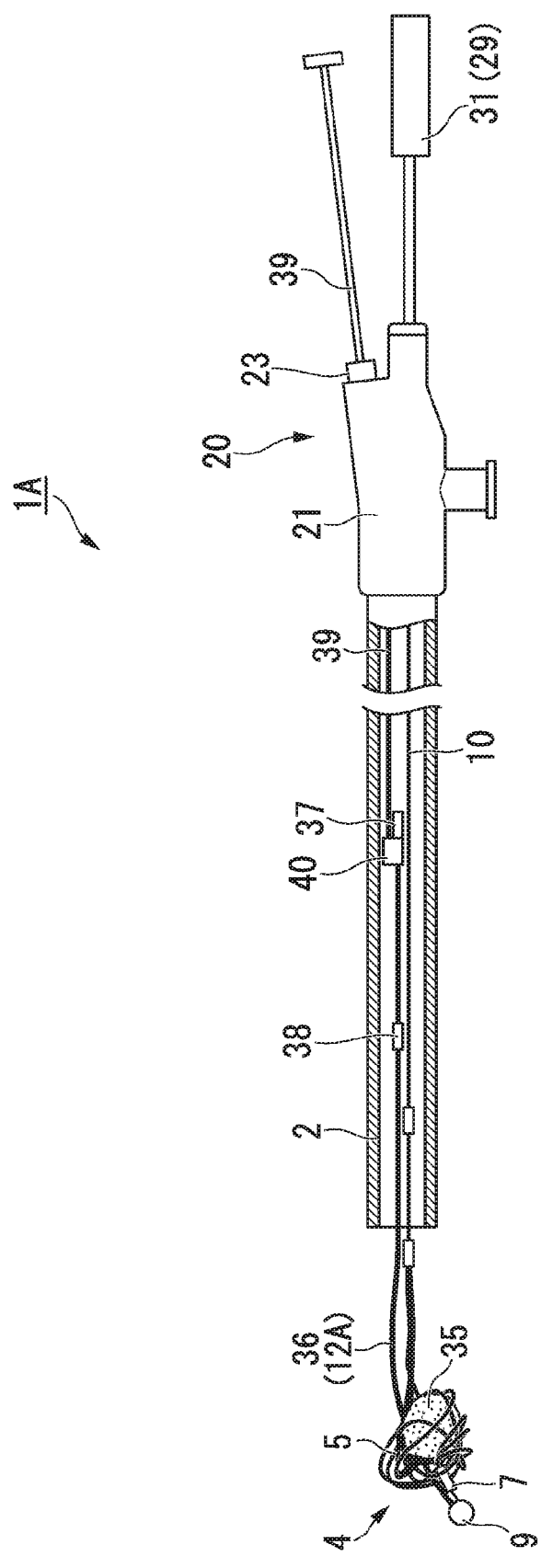
FIG. 16 is a view for describing how to use the basket-type grasping forceps.
Figure 17:
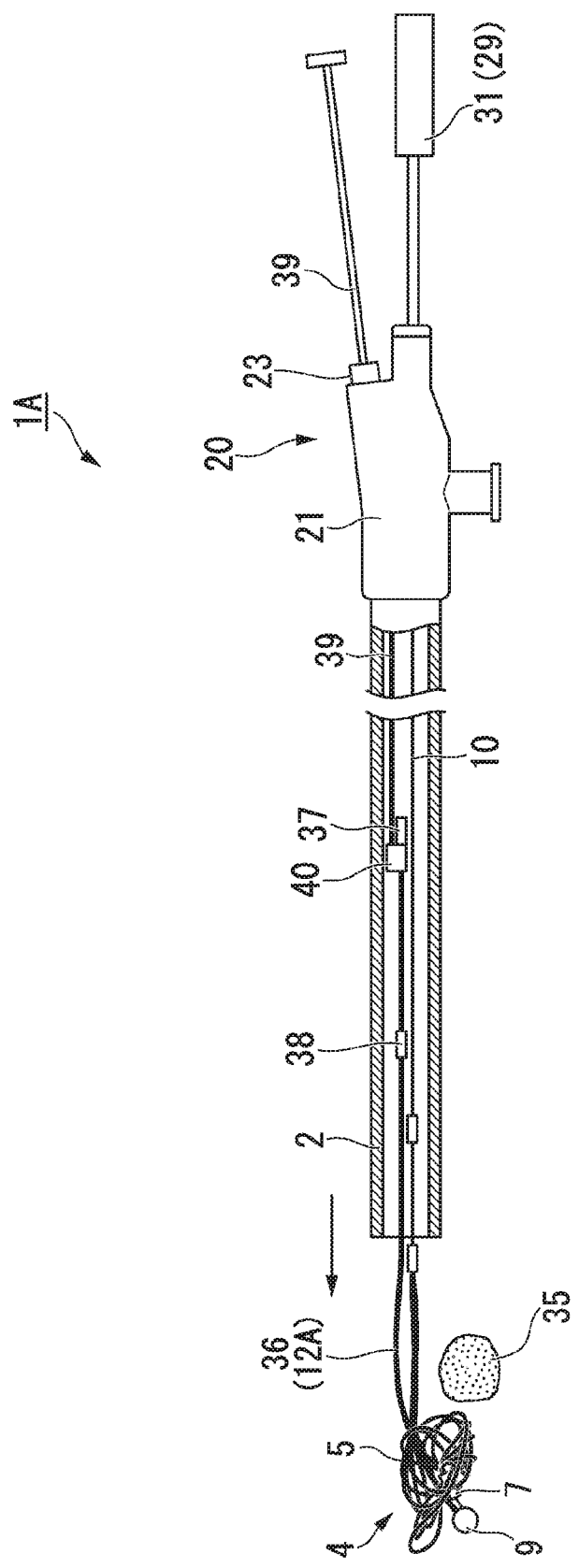
FIG. 17 is a view for describing how to use the basket-type grasping forceps.

Additionally, as described in the first embodiment, in order to collapse the basket part 4 in a substantial spindle-like shape to produce an opening, first, as illustrated in FIG. 15, the restricting wire 39 is fixed in the second port 23 in a state where the restricting wire 39 is retracted and the restricting member 40 abuts against the first locking part 37 of the center wire 12A. Subsequently, as illustrated in FIG. 16, the operating wire 10 is advanced and the proximal end of the basket part 4 is moved to the distal side. Accordingly, the position of the distal end of the basket part 4 is maintained by the body wire 36, and the position of the proximal end of the basket part 4 is moved to the distal side by the operating wire 10. As a result, as illustrated in FIG. 17, the substantial spindle-like shape of the basket part 4 collapses, similar to the first embodiment, and the same substantial circular opening as that of the first embodiment is produced toward the proximal side of the basket part 4. Accordingly, in the proximal portion of the basket part 4, the foreign matter 35 is discharged from the opening to the outside of the basket part 4. Thereafter, if the fixing of the restricting wire 39 is released by loosening the plug 26 of the second port 23 that has fixed the restricting wire 39 and the restricting wire 39 is advanced to move the center wire 12 to the front, the basket part 4 is restored to its original shape.

Third Embodiment

Figure 18:
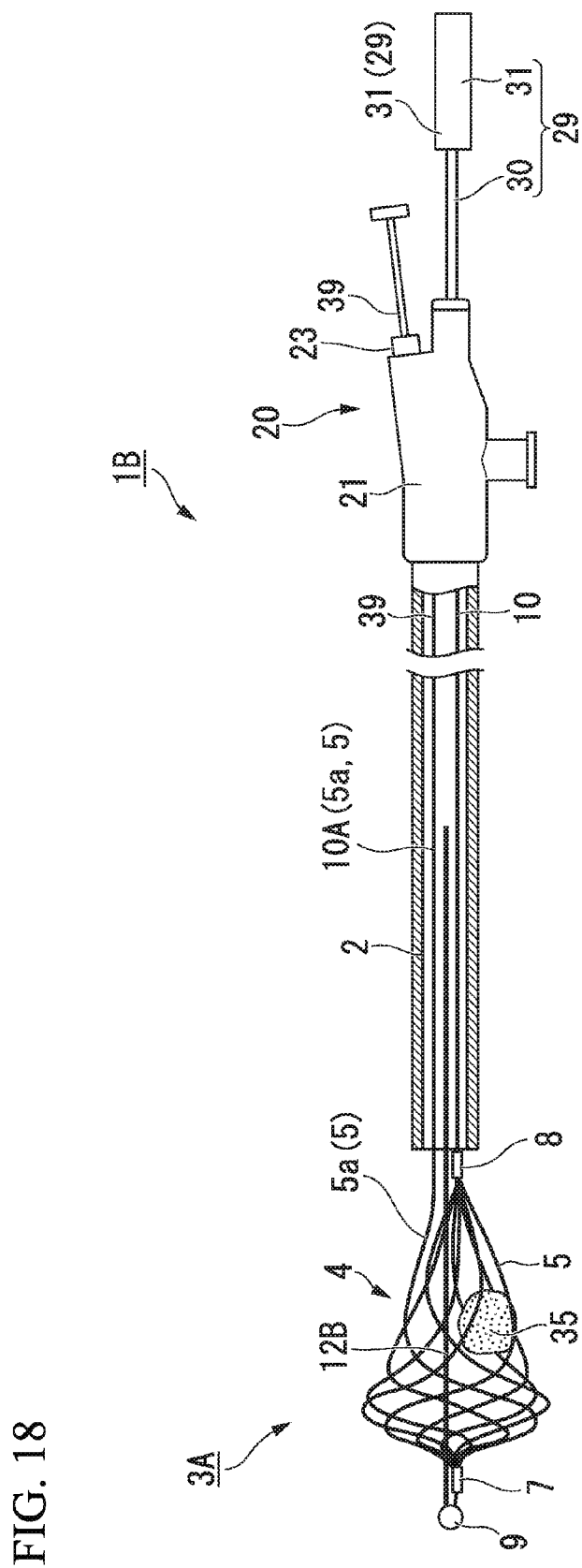
FIG. 18 is a partial sectional view illustrating basket-type grasping forceps of a third embodiment of the invention.

Next, a third embodiment of the invention will be described. FIG. 18 is a partial sectional view illustrating basket-type grasping forceps of the present embodiment.

As illustrated in FIG. 18, basket-type grasping forceps 1B of the present embodiment includes a body section 3A with a different configuration from the body section 3 of the first embodiment, instead of the body section 3 described in the first embodiment.

The body section 3A is an elongated member that has a distal end and a proximal end and is inserted through the sheath 2. The body section 3 includes the basket part 4, the operating wire 10 coupled to the basket part 4, and a center wire 12B (support member) fixed to the basket part 4.

Additionally, in the present embodiment, one (illustrated by reference sign 5a in FIG. 18) of the basket wires 5 that constitute the basket part 4 is not fixed to the proximal fixing member 8, and extends to the operating section 20 as a second operating wire 10A.

Additionally, in the present embodiment, a proximal portion of the second operating wire 10A is disposed in the second port 23 of the operating section 20. The second operating wire 10A is capable of being fixed to the operating section 20 in the present embodiment by the plug 26 (refer to FIG. 2) of the second port 23.

The center wire 12B has a distal end fixed to the proximal end of the tip member 9, similar to the first embodiment, and a proximal end thereof is disposed inside the sheath 2 unlike the first embodiment. The position of the proximal end of the center wire 12B is present within the sheath 2 even in a state where the basket part 4 is completely exposed from the distal opening of the sheath 2.

Figure 19:
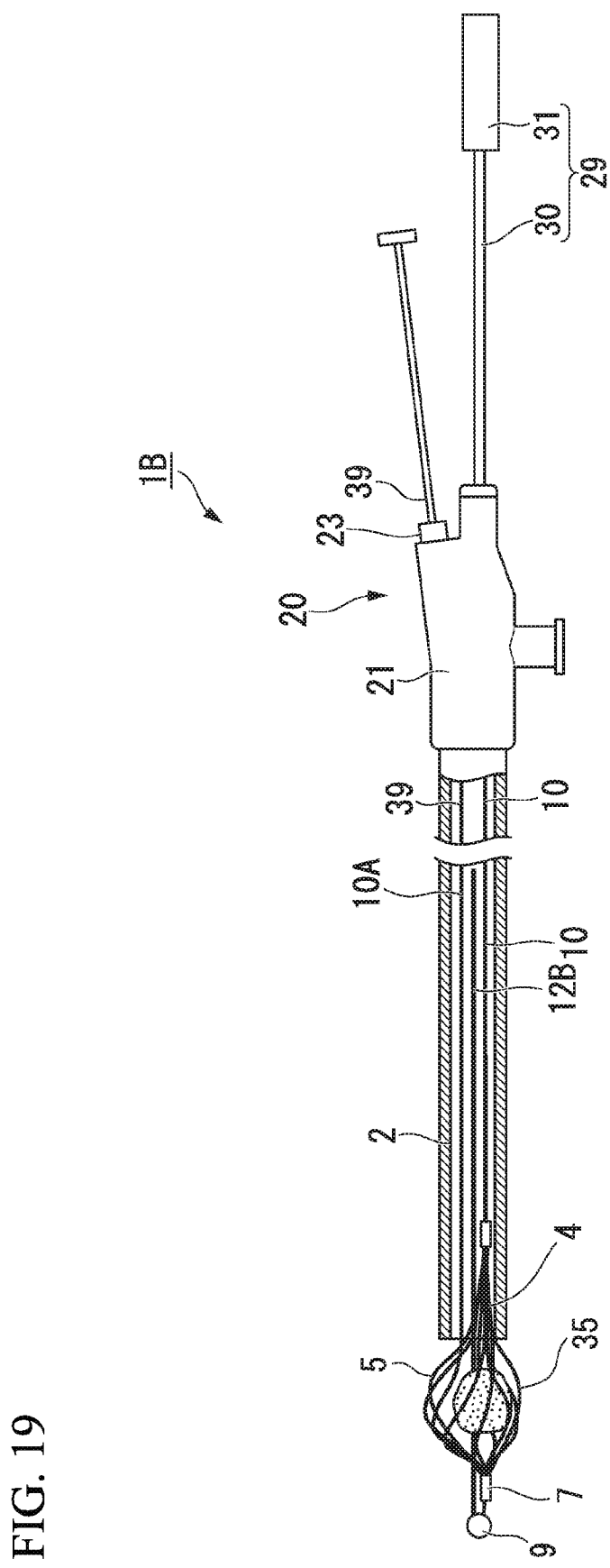
FIG. 19 is a view for describing how to use the basket-type grasping forceps.
Figure 20:
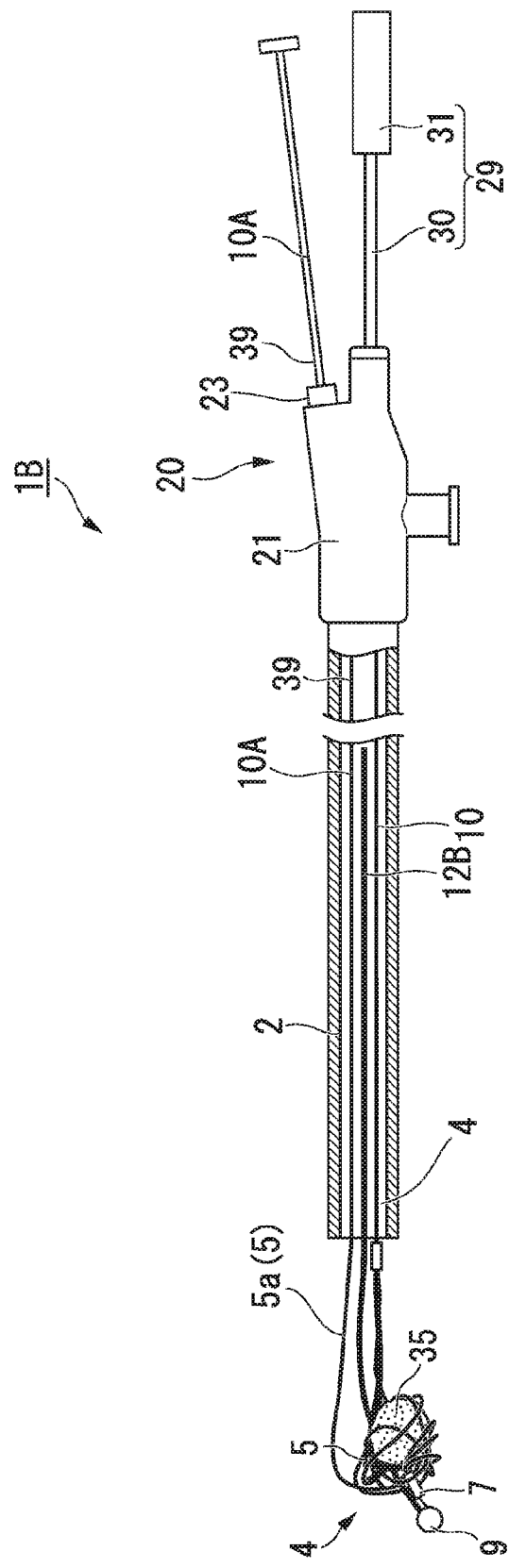
FIG. 20 is a view for describing how to use the basket-type grasping forceps.
Figure 21:
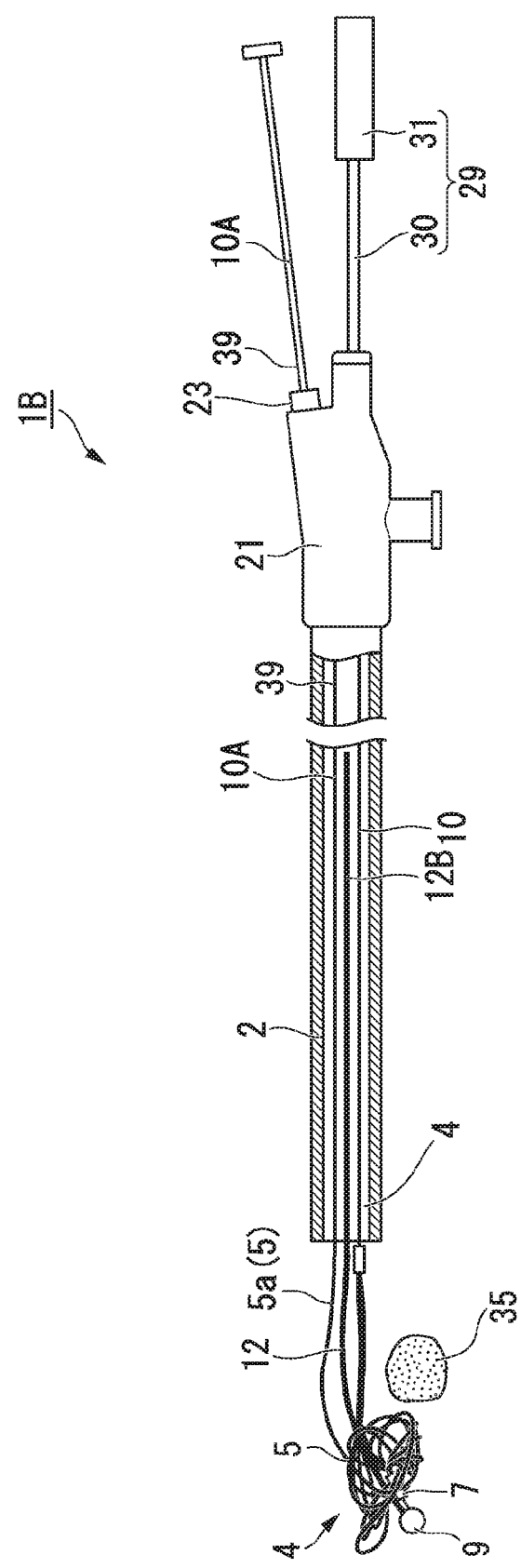
FIG. 21 is a view for describing how to use the basket-type grasping forceps.

The operation of the basket-type grasping forceps 1B of the present embodiment will be described. FIGS. 19 to 21 are views for describing how to use the basket-type grasping forceps of the present embodiment.

In the basket-type grasping forceps 1B of the present embodiment, in a state where the plug 26 of the second port 23 is loosened and the second operating wire 10A is advanceable and retractable with respect to the operating section 20, the respective basket wires 5 in the basket part 4 move together according to the advance and retraction of the operating wire 10 (first state). Additionally, in a state where the plug 26 of the second port 23 is shut and the second operating wire 10A is not advanceable and retractable with respect to the operating section 20, only basket wires that are not fixed to the second operating wire 10A in the respective basket wires 5 in the basket part 4 move according to the advance and retraction of the operating wire 10 (second state).

In the basket-type grasping forceps 1B of the present embodiment, when the foreign matter 35 is present inside the basket part 4, the foreign matter 35 can be discharged from the basket part 4 in almost the same manner as the method described in the first embodiment, in a case where the foreign matter 35 is held by the distal portion of the basket part 4 and the basket part 4 is not removable from a duct.

That is, the second operating wire 10A is fixed to the operating section 20 by the second port 23 in a state where the foreign matter 35 is held within the basket part 4, (refer to FIG. 19). Thereafter, the basket part 4 is advanced by moving the operating wire 10d to the front. Then, as illustrated in FIG. 20, basket wires excluding basket wires 5a fixed to the second operating wire 10A among the plurality of basket wires 5 are pressed to the front by the operating wire 10. Accordingly, the substantial spindle-like shape of the basket part 4 collapses, and an opening capable of discharging the foreign matter 35 is produced on the proximal side of the basket part 4. By moving the basket-type grasping forceps 1B of the present embodiment to the front in this state, as illustrated in FIG. 21, the foreign matter 35 is discharged to the outside of the basket part 4 through the opening formed in the proximal portion of the basket part 4.

Figure 22:
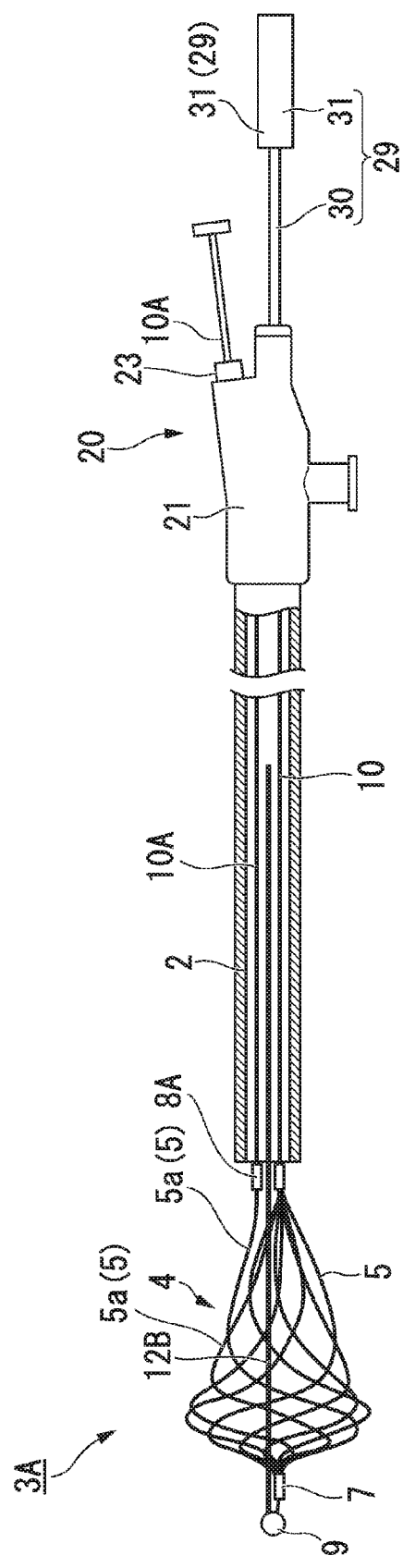
FIG. 22 is a partial sectional view illustrating another configuration example of the basket-type grasping forceps.

In addition, in the present embodiment, one or more of the plurality of basket wires 5 may be fixed to the second operating wire 10A that is separate from the basket wires 5 by techniques such as welding, brazing, and bonding, by a tubular second proximal fixing member 8A, for example, as illustrated in FIG. 22. Less than half of the plurality of basket wires 5 that constitute the basket part 4 may be fixed to the second operating wire 10A.

Additionally, in the present embodiment, instead of an aspect in which the basket wires 5 are fixed to the second operating wire 10A, wire rods that constitute the basket wires 5 may be provided to be extended to the proximal side, and thereby function as the second operating wire 10A.

Although the embodiments of the invention have been described above in detail with reference to the drawings, specific configuration is not limited to the embodiments, and design changes or the like are also included without departing from the scope of the invention.

Additionally, the constituent elements illustrated in the above-described respective embodiments can be suitably combined.

ADDITIONAL REMARK

In addition, the invention can also be expressed as follows. "An endoscopic treatment tool comprising: an insertion section; a basket part located on a distal side of the insertion section in order to house an object, the basket part being made of a plurality of basket wires and including a dense part in which the basket wires are densely arranged on a distal side and a sparse part in which the basket wires are sparsely arranged a base end side; a support member connected to a distal side of the basket part, the support member being inserted into the insertion section via the inside of the basket part; a basket wire operating section for advancing and retracting the basket wires, the operating section including a first state where all of the basket wires are simultaneously advanced and retracted, and a second state where half or more of the basket wires are moved relative to the other basket wires; and a discharge mechanism that discharges the object housed within the basket part to the outside of the basket part, the discharge mechanism including a fixing mechanism that fixes the other basket wires to the half or more of the basket wires, and moves the half or more of the basket wires relative the object within the basket part to discharge the object through the movement of the dense part or the sparse part of the half or more of the basket wires relative to other operating wires."

What is claimed is:

1. A basket-type grasping forceps for use in a body cavity, the basket-type grasping forceps comprising:
    a sheath having flexibility and formed in a tube shape;
    a plurality of basket wires having a restoring force that restores helically;
    a basket part configured to protrude and retract from a distal portion of the sheath and in which the plurality of basket wires extend helically with a gap therebetween, the basket part including:
        a proximal region in which the plurality of basket wires are sparsely arranged;
        a distal region in which the plurality of basket wires are arranged more closely than in the proximal region; and
        an internal space surrounded by the proximal region and the distal region;
    an operating wire connected to a proximal end of the basket part and is inserted into the sheath;
    a support member passing through the gap in the basket part and extending substantially parallel to the operating wire;
    a coupling member fixing a distal end of the basket part to a distal end of the support member;
    an operating section fixed to a proximal end of the sheath, the operating section having a slider connected to a proximal end of the operating wire, and the operating section including a proximal region of the support member that protrudes from an interior of the operating section to an exterior of the operating section; and
    a discharge mechanism discharging an object housed in the internal space of the basket part outside the basket part via the operating section while the basket part is configured to be disposed in the body cavity, the discharge mechanism including:

a first configuration in which the operating wire is relatively retracted along a longitudinal axis of the sheath with respect to the support member by relatively retracting the slider with respect to the support member, the first configuration being a state where: the proximal end of the basket part is positioned distally more than a distal end of the sheath, and the basket part is stretched out in an axial direction of the basket part against restoring forces of the plurality of the basket wires, and a second configuration in which the operating wire is relatively advanced along the longitudinal axis of the sheath with respect to the support member by relatively advancing the slider with respect to the support member, the second configuration being a state where: the proximal end of the basket part is positioned distally more than the distal end of the sheath, and the basket part is deformed in the axial direction of the basket part such that the gap in the proximal region of the basket part has a substantial round shape against the restoring forces of the plurality of the basket wires.

2. The basket-type grasping forceps according to claim 1, wherein the discharge mechanism moves the proximal end of the basket part in a direction of approach to the distal end of the support member, thereby moving the object inside the basket part from the distal region of the basket part to the proximal region thereof.

3. The basket-type grasping forceps according to claim 1, wherein the support member includes:
a body wire that is coupled to the distal end of the basket part and extends to the vicinity of the proximal end of the basket part;
a first locking part that is fixed to a proximal end of the body wire and has a larger outside dimension than the external diameter of the body wire; and
a second locking part that is fixed to the body wire at a position apart from the first locking part further to a distal side than the first locking part and has a larger outside dimension than the external diameter of the body wire, the operating section includes:
a restricting member that has a through-hole of a diameter such that the body wire is advanceable and retractable through the through-hole and is disposed between the first locking part and the second locking part in a state where the body wire is inserted through the through-hole; and
a restricting wire that has a distal end part fixed to the restricting member and extends to the operating section through the inside of the sheath, and movement of the body wire to a proximal side with respect to the sheath is restricted by fixing the advance/retraction position of the restricting wire in a state where the restricting member abuts against the second locking part, and movement of the body wire to a distal side with respect to the sheath is restricted by fixing the advance/retraction position of the restricting wire in a state where the restricting member abuts against the first locking part.

4. The basket-type grasping forceps according to claim 1, wherein the basket wires are made of a shape memory alloy.

5. The basket-type grasping forceps according to claim 1, wherein the basket part includes a binding part that binds distal portions of the basket wires,
the coupling member is coupled to a distal side of the binding part with a wire, and
the support member passes through the inside of the basket part at a position offset further in an outer circumferential direction than the centerline of the basket part with respect to the binding part.

6. The basket-type grasping forceps according to claim 1, wherein each of the plurality of basket wires is composed of one substantial linear shape and is configured so that a pitch of a helical shape of the basket wire becomes narrower toward a distal side.

7. The basket-type grasping forceps according to claim 1, wherein the plurality of basket wires have a restoring force such that a substantial spindle-like shape is maintained by the plurality of basket wires.

* * * * *